(12) United States Patent
Weizmann

(10) Patent No.: US 8,184,669 B2
(45) Date of Patent: May 22, 2012

(54) SYSTEM AND METHOD TO REGULATE HIGH CURRENT RADIATION SOURCES

(75) Inventor: Ofer Weizmann, Kiryat Motzkin (IL)

(73) Assignee: Lumenis, Ltd., Yokneam (IL)

( * ) Notice: Subject to any disclaimer, the term of this patent is extended or adjusted under 35 U.S.C. 154(b) by 0 days.

(21) Appl. No.: 13/150,570

(22) Filed: Jun. 1, 2011

(65) Prior Publication Data

US 2011/0228801 A1    Sep. 22, 2011

Related U.S. Application Data

(63) Continuation of application No. 12/409,274, filed on Mar. 23, 2009, now Pat. No. 7,961,767.

(51) Int. Cl.
- *H01S 3/30* (2006.01)
- *H01S 3/13* (2006.01)
- *H01S 3/00* (2006.01)

(52) U.S. Cl. ............ 372/29.015; 372/8; 372/38.07

(58) Field of Classification Search .......... 372/29.011, 372/29.015, 38.01, 38.02, 38.07, 8
See application file for complete search history.

(56) References Cited

U.S. PATENT DOCUMENTS

| | | | |
|---|---|---|---|
| 5,048,033 A | 9/1991 | Donahue et al. | |
| 5,626,631 A | 5/1997 | Eckhouse | |
| 6,418,154 B1 * | 7/2002 | Kneip et al. | 372/25 |
| 7,108,689 B2 | 9/2006 | Eckhouse et al. | |
| 7,203,213 B2 * | 4/2007 | Anderson et al. | 372/38.07 |
| 7,961,767 B2 * | 6/2011 | Weizmann | 372/38.02 |
| 2005/0129075 A1 | 6/2005 | Anderson et al. | |
| 2010/0238961 A1 | 9/2010 | Weizmann | |

FOREIGN PATENT DOCUMENTS

EP    0817544    1/1998

OTHER PUBLICATIONS

European Patent Office, "European Search Report", mailed Mar. 7, 2012, Published in: EP.

* cited by examiner

*Primary Examiner* — Armando Rodriguez
(74) *Attorney, Agent, or Firm* — Fogg & Powers LLC

(57) ABSTRACT

Disclosed is a high current radiation system. The system includes a high current radiation source to generate radiation and an analog circuit to generate, based, at least in part, on an input signal representative of the present current level delivered to the high current radiation source and a user-controlled input representative of a desired current level, an output signal to control a current level to be delivered to the high current radiation source. The system further includes a current driver to control the current delivered to the high current radiation source based, at least in part, on the output signal of the analog circuit.

14 Claims, 7 Drawing Sheets

SYSTEM AND METHOD TO REGULATE HIGH CURRENT RADIATION SOURCES

CROSS REFERENCE TO RELATED APPLICATION

This application is a continuation application of U.S. patent application Ser. No. 12/409,274, filed Mar. 23, 2009, entitled "System and Method to Regulate High Current Radiation Sources," the content of which is hereby incorporated by reference in its entirety.

BACKGROUND

The present disclosure relates to a current regulation system and method, and more particularly to a current regulation system and method to regulate high current provided to radiation sources such as, for example, an Intense Pulsed Light (IPL) source or a laser source.

Generally, current regulators are implemented using programmable components such as processor-based devices, Field-Programmable Gate Arrays (FPGA), etc. Such components are generally relatively expensive. Furthermore, use of programmable devices/components generally results in relatively complex implementations.

SUMMARY

In one aspect, a high current radiation system is disclosed. The system includes a high current radiation source to generate radiation, an analog circuit to generate, based, at least in part, on an input signal representative of the present current level delivered to the high current radiation source and a user-controlled input representative of a desired current level, an output signal to control the current level to be delivered to the high current radiation source, and a current driver to control the current delivered to the high current radiation source based, at least in part, on the output signal of the analog circuit.

Embodiments of the system may include one or more of the following features.

The analog circuit may include an analog comparator implemented using at least one operational amplifier. The analog comparator may be configured to generate a logical high signal when a voltage level of the user-controlled input exceeds a voltage level of the input signal representative of the present current level delivered to the high current radiation source, and generate a logical low signal when the voltage level of the user-controlled input is below the voltage level of the input signal representative of the present current level delivered to the high current radiation source.

The high current radiation source may include one or more of, for example, an Intense Pulsed Light (IPL) device and/or a laser device.

The current driver may include a power transistor to enable flow of high current level provided from a power source to the radiation source when the power transistor is actuated by a logical high signal, and to disable current flow through the power transistor when the power transistor is actuated by a logical low signal. The power transistor may include an Insulated-Gate Bi-Polar Transistor (IGBT).

The system may further include a sensor to measure the present current level delivered to the radiation source. The input signal representative of the present current level delivered to the radiation source may be generated, at least in part, based on the present current level delivered to the radiation source measured by the sensor.

The system may further include a simmer board to trigger the radiation source.

The analog circuit may be implemented without any programmable devices.

In another aspect, a method to regulate the current level delivered to a high-current radiation source is disclosed. The method includes generating, using an analog circuit, an output signal to control a current level to be delivered to the high current radiation source based on an input signal representative of a present current level delivered to the high current radiation source and a user-controlled input representative of a desired current level, and controlling current delivered to the high current radiation source based, at least in part, on the output signal of the analog circuit.

Embodiments of the method may include any of the above described features of the system, as well as one or more of the following features.

Generating, using the analog circuit, the output signal may include generating using an analog comparator implemented using at least one operational amplifier the output signal to control the current delivered to the high current radiation source.

Controlling the current may include actuating a power transistor to control the current flow from a power source to the high current radiation source using the generated output signal such that the current flow from the power source is enabled when the actuating signal is a logical high and the current flow from the power source is disabled when the actuating signal is a logical low.

The method may further include measuring, using a sensor, the present current level delivered to the radiation source. The input signal representative of the present current level delivered to the radiation source may be generated, at least in part, based on the present current level delivered to the radiation source measured by the sensor.

The method may further include triggering the radiation source using a simmer board.

Details of one or more implementations are set forth in the accompanying drawings and in the description below. Further features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Described herein are high current radiation systems and methods to regulate current delivered to such radiation sources. In some embodiments, a high current radiation system includes a high current radiation source to generate radiation, and an analog circuit to generate, based, at least in part, on an input signal representative of the present current level delivered to the high current radiation source and a user-controlled input representative of a desired current level, an output signal to control the current level to be delivered to the high current radiation source. The system further includes a current driver to control the current delivered to the high current radiation source based, at least in part, on the output signal of the analog circuit. In some embodiments, the analog circuit may include an analog comparator implemented using at least one operational amplifier. The analog circuit may be implemented without any programmable devices.

Figure 1:
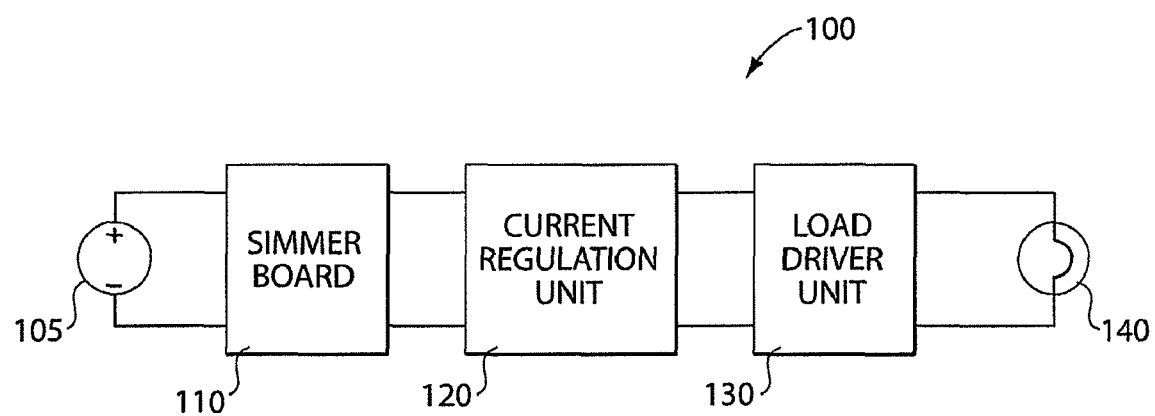
FIG. 1 is a block schematic diagram of a radiation system.

Referring to FIG. 1, a block schematic diagram of a radiation system 100 is shown. The system 100 includes a simmer board 110 to trigger the radiation source (i.e., make it conductive and ready for operation), a current regulation unit 120 to generate control signals to regulate the current provided to a load (e.g., an IPL lamp) and a load driver unit 130 which, in response to the control signals received from the current regulation unit 120, regulates the current flow (i.e., drives the load by, for example, turning on and off a switching device through which current is provided to the load).

The system 100 further includes a high current radiation source 140 to generate radiation emissions that are directed to the areas to be treated (e.g., skin tissue of a patient). In some embodiments, the high current radiation source 140 is an Intense Pulsed Light source. Such a light source may include an incoherent light source such as a gas filled linear flash lamp. The spectrum of light emitted by a gas filled linear flash lamp may depend on current density, the type of glass envelope material and gas mixture used in the tube. For large current densities (e.g., 3000 A/Cm$^2$ or more) the spectrum may be similar to a black body radiation spectrum. Typically, most of the energy is emitted in the 300 to 1300 nm wavelength range. Further details regarding IPL sources and corresponding implementations and applications are provided, for example, in U.S. Pat. No. 5,626,631, entitled "Method and Apparatus for Therapeutic Electromagnetic Treatment" and in U.S. Pat. No. 7,108,689, entitled "Method and Apparatus for Electromagnetic Treatment of the Skin, including Hair Depilation," the contents of both of which are hereby incorporated by reference in their entireties. An example of a suitable IPL source is a Xenon flash lamp that is controlled to generate intense incoherent pulses that have durations of, for example, a few microseconds to a few milliseconds.

In some embodiments, the radiation source may include laser devices configured to operate in either continuous or pulsed mode. Suitable laser devices include, for example, Nd:YAG laser devices, Nd:YLF laser devices, Yb:YAG laser devices, etc. Other types of radiation sources, such as radio frequency sources, ultrasound sources, etc., may also be used.

As further shown in FIG. 1, power for the high current radiation source 140 is provided by the power source 105. The power source 105 may include standard electrical outlets, one or more batteries, an electric generator, etc.

Figures 1, 2A:
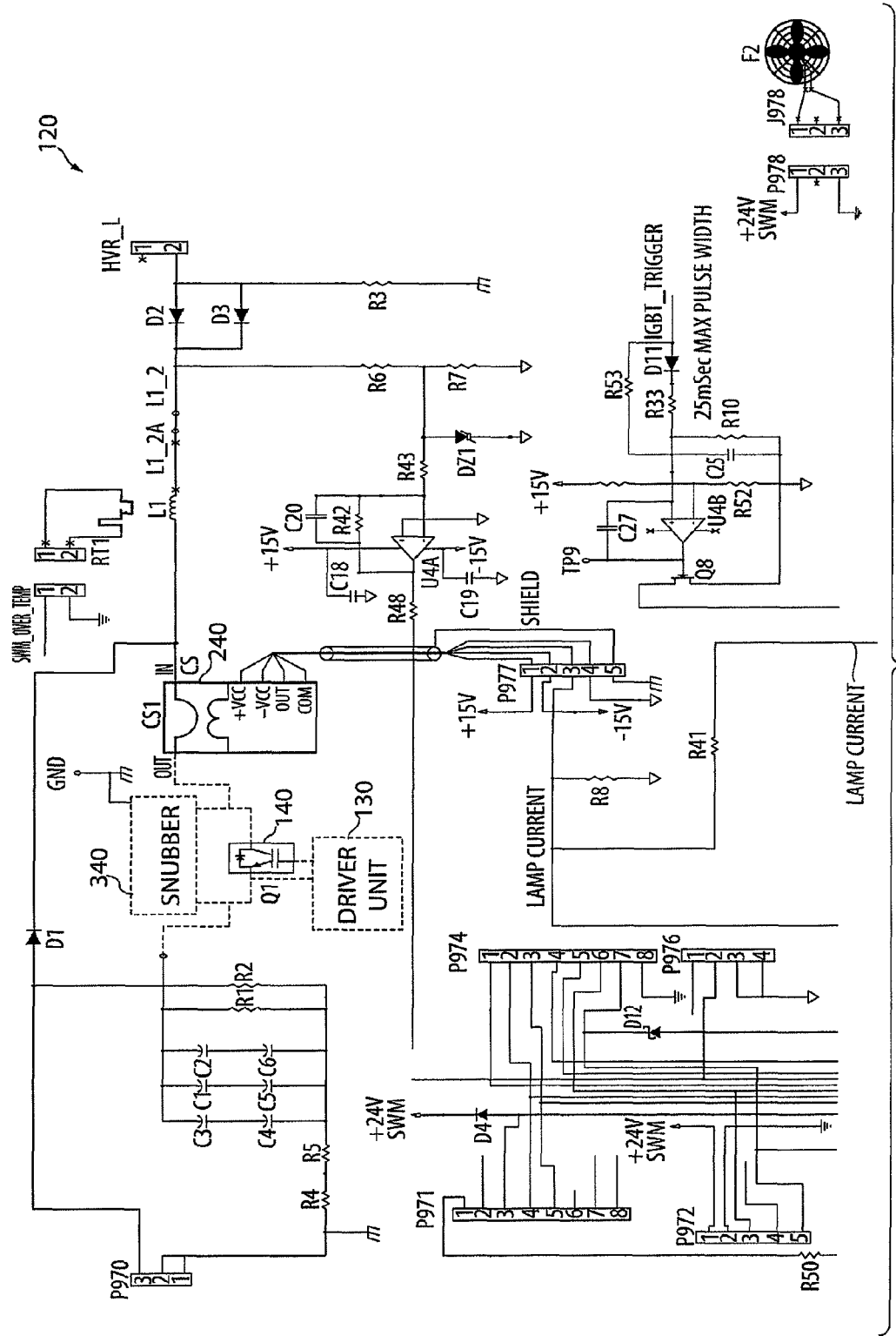
FIG. 2A is a circuit schematic diagram of an implementation of a current regulation unit included in the radiation system of FIG. 1.

The current regulation unit 120, schematically depicted in FIG. 1, is configured to regulate the current/voltage level of the current/voltage provided by the power source 105 based, at least in part, on user-controlled input representative of current level required or desired by the user, and a signal representative of the actual present current/voltage level applied to the radiation source. The current regulation unit is further configured, among other things, to generate, based on the aforementioned inputs, a control output signal that regulates (or actuates) the driver unit (which may include one or more switching devices). Referring to FIG. 2A, a circuit schematic diagram of an implementation of the current regulation unit 120 is shown. The current regulation unit 120 includes an analog current regulator circuit 210 that receives a user-controlled input representing a desired current that is to be provided to the radiation source and a signal representing the actual present current flowing in the radiation source, and based on those inputs generates a control signal 230 that is used to actuate the driver unit 130 of the system 100. Thus, the current regulation unit 120 is implemented without using any programmable devices to control/regulate the high current that is provided to the radiation source 140.

Figures 2, 2A:
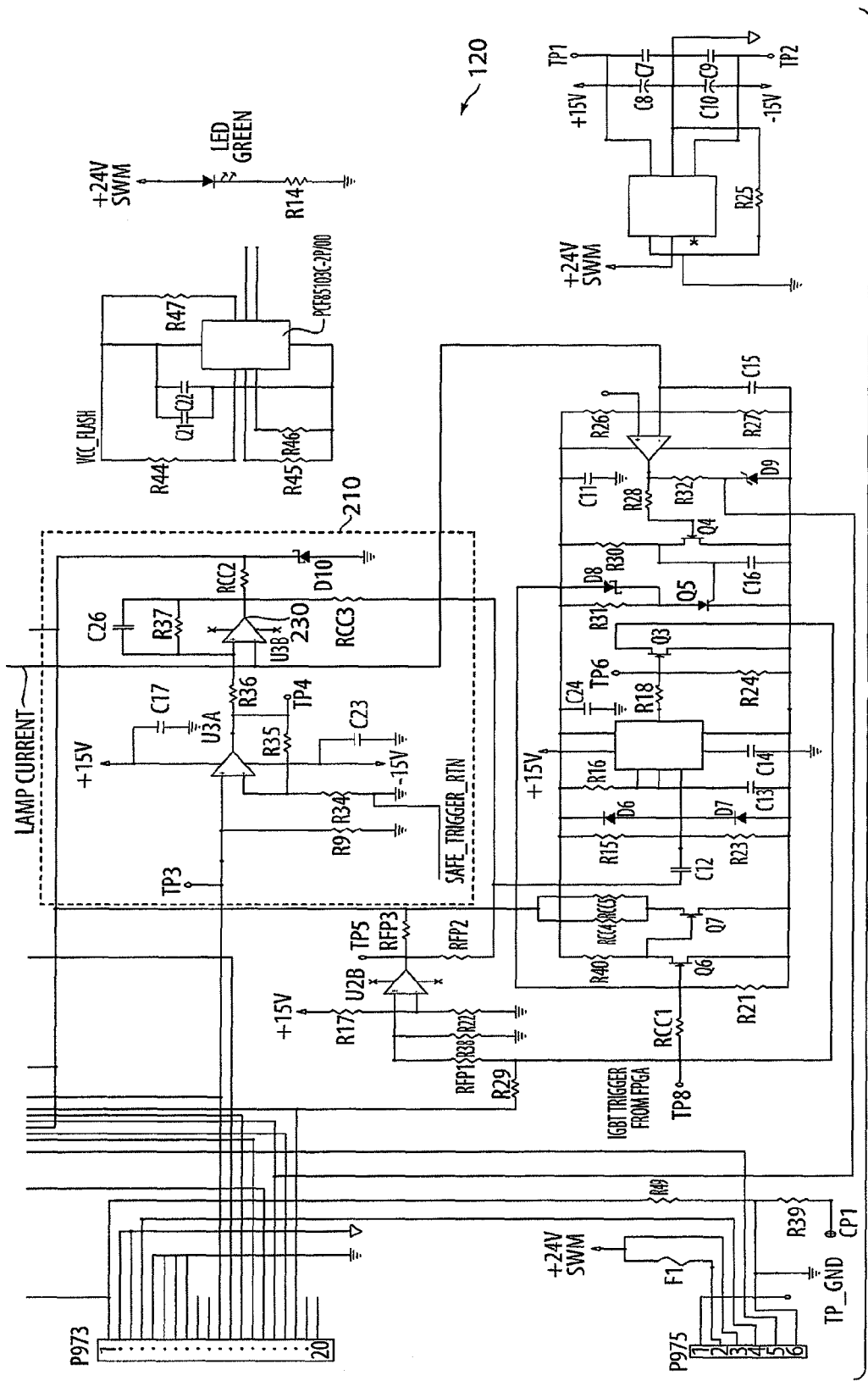
Figure 2B:
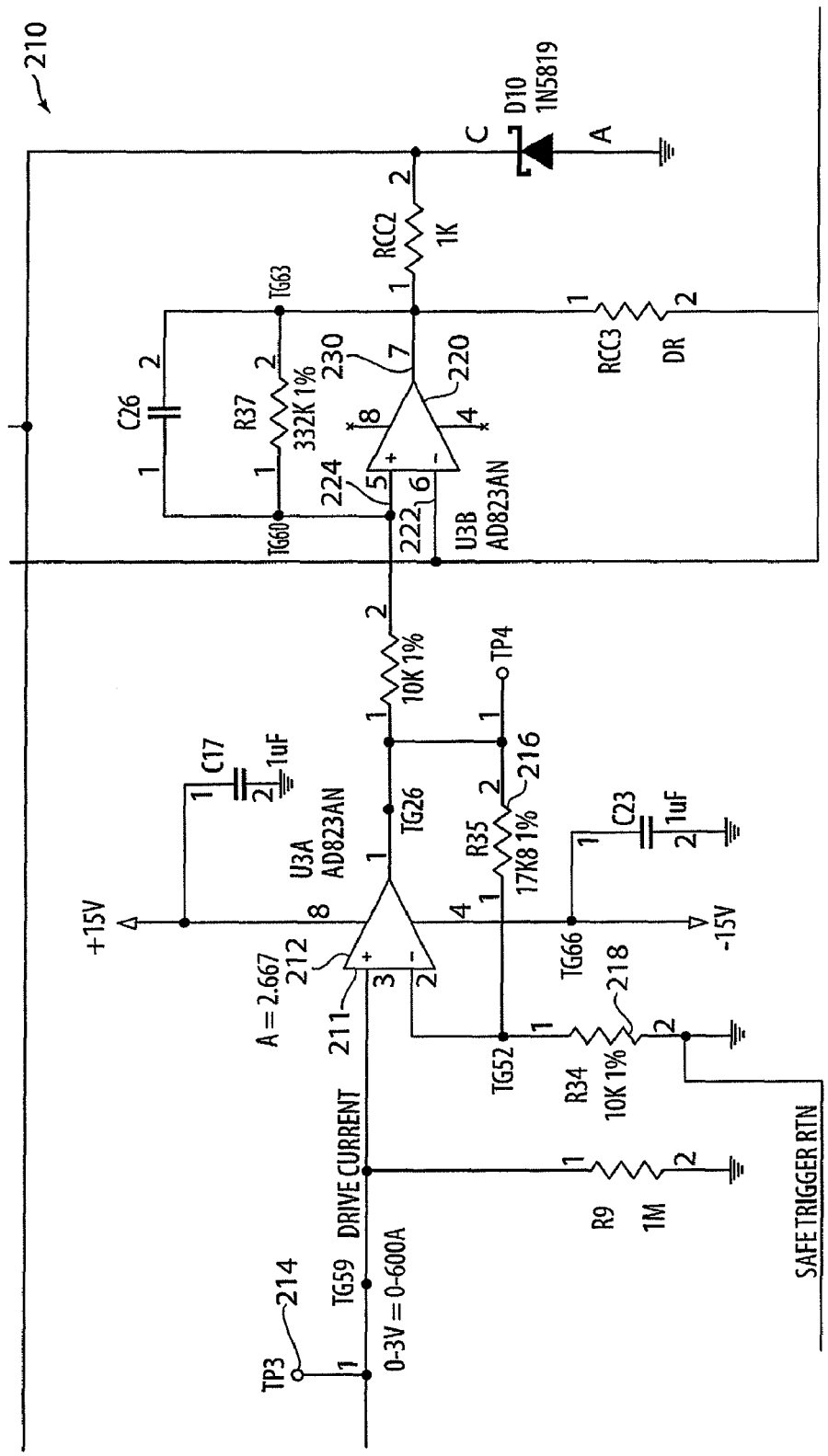
FIG. 2B is an enlarged circuit schematic diagram of the current regulator analog circuit shown in FIG. 2A.

Referring to FIG. 2B, an enlarged circuit schematic diagram of the analog current regulator circuit 210 is shown. The analog circuit 210 includes, in some embodiments, an amplifier, such as an operational-amplifier-based arrangement, to perform an initial amplification to amplify the user-controlled input signal representative of the current level required to be applied to the radiation source. As shown, the amplifier depicted in FIGS. 2A and 2B is implemented using an operation amplifier 212 (marked U3A). The user-controlled input signal is provided at the terminal 214 (marked TP3) in FIG. 2B, and may be generated through a user-interface (e.g., buttons, switches, keypad, etc.) that cause a signal level at a particular voltage range to be produced in response to input from the user. In some embodiments, the signal produced at terminal 214 has a level range of 0-3V. This range corresponds to the current range that flows through the radiation source. For example, if the maximum current that may be set to flow through the radiation source is 600 A, an input signal of 3V (produced based on user-controlled inputs provided through the user interface) may represent a desired radiation source current of 600 A. Thus, under those circumstances, a signal of 1.5V at the terminal 214 will correspond to a desired current level of 300 A.

The input signal representative of the desired current level is provided as input to the amplifier implemented using the operational-amplifier 212. As will become apparent below, in some embodiments, the input signal representative of the current flowing through the radiation source (i.e., the actual current level) may have a different range of values than the signal level range of the user-controlled input signal representative of the desired current required to be provided to the radiation source. For example, in the implementation depicted in FIGS. 2-4, the signal representative of the actual current of the radiation source may have a signal range of 0-8V (e.g., 8V may correspond to 600 A). Accordingly, to ensure that the signal level range of the user-controlled input signal matches the signal level range of the signal representative of the actual current level, the amplifier implemented using the operational amplifier 212 effectively transforms the input signal (provided to it at the positive terminal 211 of the amplifier 212) to a level range that is in substantially the same level range as the signal representative of the actual current level of the radiation source. Thus, in the example depicted in FIG. 2B, to transform the signal level of the signal at terminal 214 from its approximately 0-3V range to the approximately 0-8V range of the signal representative of actual current level, the operational-amplifier 212 is required to amplify the input signal level provided to it at the terminal 211 by a factor of approximately 2.667 (corresponding to 8V/3V=2.667 V/V). To control the level of amplification realized using the operational amplifier 212, the operational amplifier 212 is arranged in a non-inverting configuration such that the input terminal 214 is electrically coupled to the positive terminal of the operational amplifier 212. Resistors 216 (R35 in FIG. 2B) and 218 (R34 in FIG. 2B) are connected to form the negative feedback loop from the output of the operational amplifier 212 to the negative input terminal of the operational amplifier 212. The values of the resistors 216 and 218 may be chosen so that, in some embodiments, the operational amplifier has a gain of approximately 2.667 V/V. For example, in some embodiments, the gain is established according to the relationship, A=1+R35/R34 (a resistance values of 17.8KΩ for R35 and 10KΩ, used in the implementation of FIG. 2B, would yield a gain value of 2.78 which approximates a gain of 2.667). Suitable operational amplifiers that may be used in the implementation of the amplifier stage of the current regulation circuit (as well as throughout the implementation described herein) include commercially available amplifiers like those manufactured by, for example, Analog Devices, Texas Instruments, Linear Technology, etc. As shown in FIG. 2B, in some embodiments, the operational-amplifiers used include Analog Devices AD823AN operational amplifiers.

The amplified output of the user-controlled input signal (e.g., based on user-specified input) is electrically communicated to a comparator implemented, for example, using an operational amplifier 220 (marked U3B). The comparator is configured to generate, based, at least in part, on the amplified signal outputted by the operational amplifier 212 and based on the input signal representative of the present actual current level of the radiation source, an output signal to control the current level to be delivered to the high current radiation source. As will become apparent below, the outputs produced may be constant logical high or logical low voltages (i.e., the output produced by the operational amplifier 220 can be one of two voltage levels). The produced output signal of the operational amplifier 220 (e.g., "high" or "low" voltage levels) can then used to actuate a switching device(s). As will further become apparent below, in the embodiments described herein, the signal 230 generated by the comparator actuates the load driver unit 130 which acts as a switch to control delivery of current (power) to the radiation source.

Thus, as shown, in some embodiments, the negative terminal 222 (marked as terminal 6) of the operational amplifier 220 is electrically coupled (via resistor R41 and the connector P977 shown in FIG. 2A) to the output of a current sensor 240 (shown in FIG. 2A) such as, for example, an amperemeter. The sensor 240 measures the current flowing (directed) through the high current radiation source 140 and generates a signal representative of that measured current. In some embodiments, the measured signal is converted (normalized) to a signal in the range of 0-8 V. Thus, a value of 8V of the normalized signal may represent, for example, a current level of 600 A passing through the radiation source. In some embodiments, the normalization operations may be performed to produce output signal having different ranges (i.e., different from the 0-8V range) and/or with respect to different current ranges corresponding to the currents that may pass through the high current radiation source.

Electrically coupled to the positive terminal 224 (also marked as terminal 5) of the operational-amplifier 220 is the amplified output from the operational amplifier 212 that represents the user-desired current level that should be flowing in the high current radiation source.

The comparator circuit receives a generally constant user-controlled signal (i.e., constant until such time that the user provides input indicating a different desired current level for the high current radiation source) to cause the current flowing through the high current radiation source to converge to a value substantially equal to the value desired by the user. Specifically, if the actual current level flowing through the high current radiation source, as indicated by the input signal that is electrically coupled to the input terminal 222 of the operational amplifier 220, is below the signal voltage level provided through the input terminal 224, the output of the operational amplifier 220 (i.e., the operation amplifier used to implement the comparator) will go high. Consequently, the driver unit 130 regulating the flow of current into the high current radiation source will be actuated to cause current to flow to the radiation source 140, thus causing an increase in the current level passing to the radiation source in a particular period of time (e.g., one second) and in effect increasing the effective current level flowing through the radiation source.

On the other hand, when the current level flowing through the radiation source exceeds the desired current level indicated by the user (this may also intermittently occur if the signal actuating the switching device regulating current flow through the radiation source remains closed long enough to enable the current level to exceed the desired current level), the sensor 240 will generate a signal representative of that current level (which is now higher than what the desired level is). As a result, the signal level at the negative terminal 222 will be higher than the signal level at the terminal 224 of the operational amplifier 220. Consequently, the output of the operational amplifier 220 will be set to a logical low output (e.g., 0V). Accordingly, the actuating signal provided to the driver 130 (including, e.g., an actuation circuit arrangement 310 shown in FIG. 3) will cause the switching device (e.g., an IGBT transistor) of the driver unit to open, thus stopping the flow of current (or application of voltage) from the power source 105 to the radiation source 140. As a result, the current level passing through the radiation source in a given time period will begin to decrease, causing the current level to converge back to the desired current level. If the current level drops again below the desired current level, the comparator will again generate a logical high level signal, causing the driver unit 130 (or any other implemented switching device to drive the radiation source) to be actuated such that current is again provided to the radiation source.

As further shown, in some embodiments, a resistor R37 may be electrically coupled between the positive terminal 224 of the comparator (implemented using the operational amplifier 220) and its output terminal (marked as terminal 7). The value of the resistor R37 may be used to control the comparator's hysteresis behavior to prevent excessive changes in the state (High/Low) of the comparator. Implementation of hysteresis behavior in the comparator may result in controlled deviations of the current flowing in the radiation source. For example, in some embodiments, the value of the resistor in the positive feedback path of the comparator can be selected so that the resultant current deviations from the target current is ±50 A (e.g., if the target current is 500 A, the resistor R37 can be selected to have a value that will result in hysteresis behavior causing current swings of between 450-550 A). Implementation of hysteresis behavior reduces the switching frequency of the switching devices/components (e.g., the IGBT switch) in the implementation depicted in FIGS. 2-4.

Figure 3:
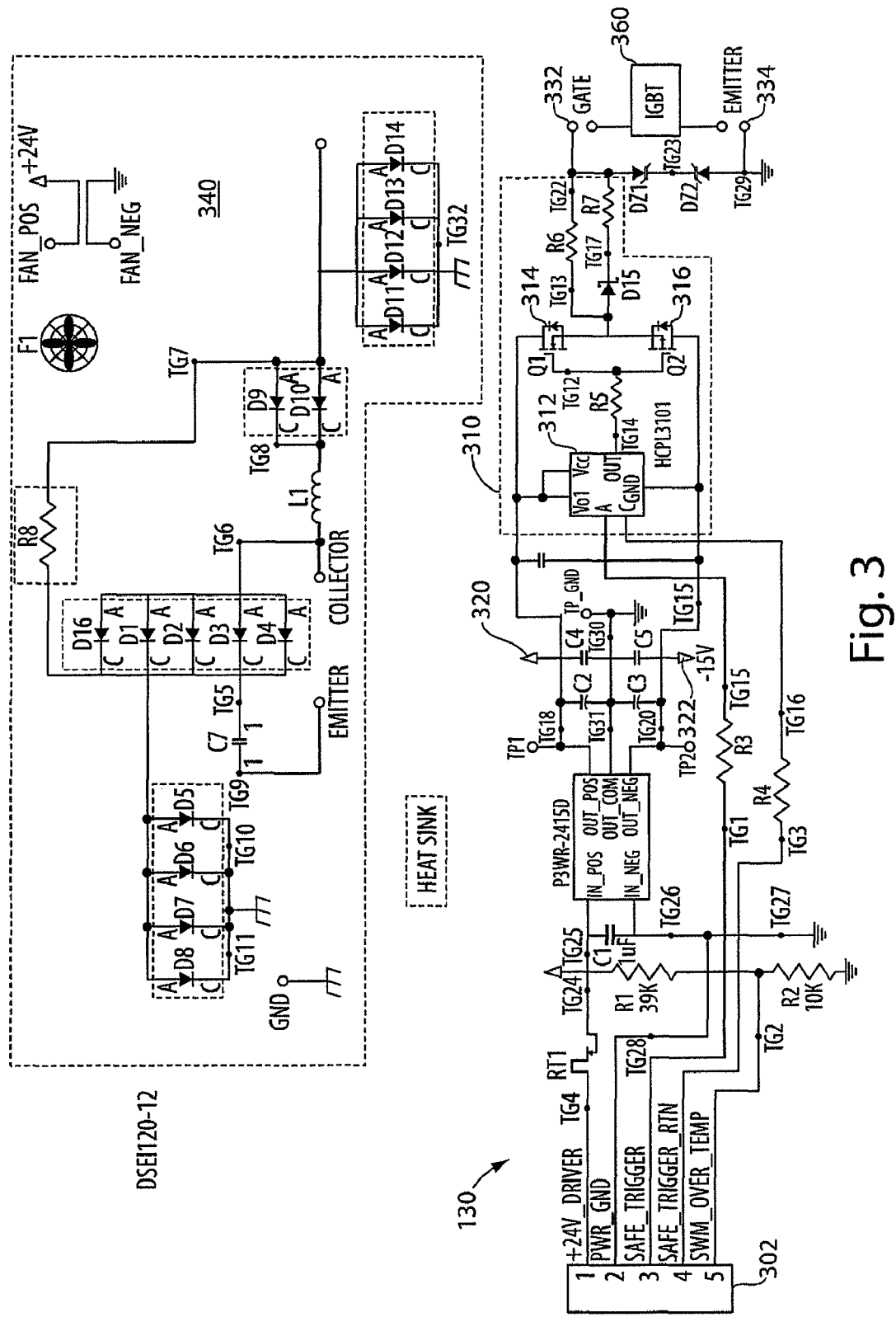
FIG. 3 is a circuit schematic diagram of a load driver unit such as the one shown in FIG. 1.

Referring to FIG. 3, a circuit schematic diagram of a load driver unit 130 is shown (a schematic representation of the driver unit 130 relative to the load 140 and the circuit schematic of the current regulation unit 120 also appears in FIG. 2A). In some embodiments, the driver unit 130 is implemented using an Insulated-Gate Bi-Polar Transistor, or IGBT 360, that electrically couples the power source 105 to the radiation source. Other types of high-power switching devices (e.g., high power transistors) configured to enable transfer of high power, may also be used. The IGBT is controlled (actuated) using the actuation circuit arrangement 310. The actuation circuit receives the controlled signal 230 (or some filtered/attenuated version thereof) that is coupled to the driver unit 130 via the pin 3 of a connector 302 (also marked as component P961). The signal 230 actuates the actuation circuit arrangement 310 which in turn actuates the IGBT to close the IGBT (i.e., make it conductive to thus enable power transfer) or open the IGBT (i.e., make it non-conductive to disable power transfer).

Specifically, the actuation circuit arrangement 310 may include a gate driver optocoupler 312, such as an HCPL3101 gate optocoupler, to receive the control signal from the current regulator (e.g., the control signal 230) and, based on the received signal, drive the IGBT accordingly. The gate driver 312 interfaces between the received signal and the IGBT to generate the actuation signals needed to drive the IGBT in accordance with the control signal 230. Electrically coupled to the gate driver 312 are an nFET transistor 314 (i.e., an re-channel transistor, marked as Q1) connected at its drain and source to the respective drain and source of a pFET transistor 316 (i.e., a p-channel FET transistor, marked as Q2). When a logical high signal is applied by the gate driver 312 (i.e., when the gate driver 312 is actuated by a high-signal from the analog-based regulator circuit) to the gate of the transistor 314, the nFET transistor will become conductive, thus coupling the +15V source to the GATE terminal 332 that is coupled (in operation) to the gate of the IGBT (the GATE terminal will be at +15 relative to the EMITTER terminal 334). This will cause the IGBT to become conductive and enable high current to flow through the power IGBT transistor to the radiation source 140. During this time, the pFET transistor will be open (i.e., non-conductive). On the other hand, if the actuating signal 230 produced by the current regulation unit corresponds to a low signal, the gate driver 312 will generate, in response, a negative driving signal to cause the transistor 316 to become conductive, while causing the transistor 314 to be non-conductive, thus electrically coupling the −15V source 322 to the GATE terminal 332. This, in turn, will cause the IGBT power transistor to effectively be switched off, thus preventing high current from flowing to the radiation source.

Also shown in FIG. 3 is a snubber circuit 340 configured to provide electrical protection from overload and/or surge conditions. A schematic representation of the snubber circuit 340 electrically connected to the radiation source 140 also appears in the circuit schematic of FIG. 2A depicting, among other things, the current regulation unit 120.

Figure 4:
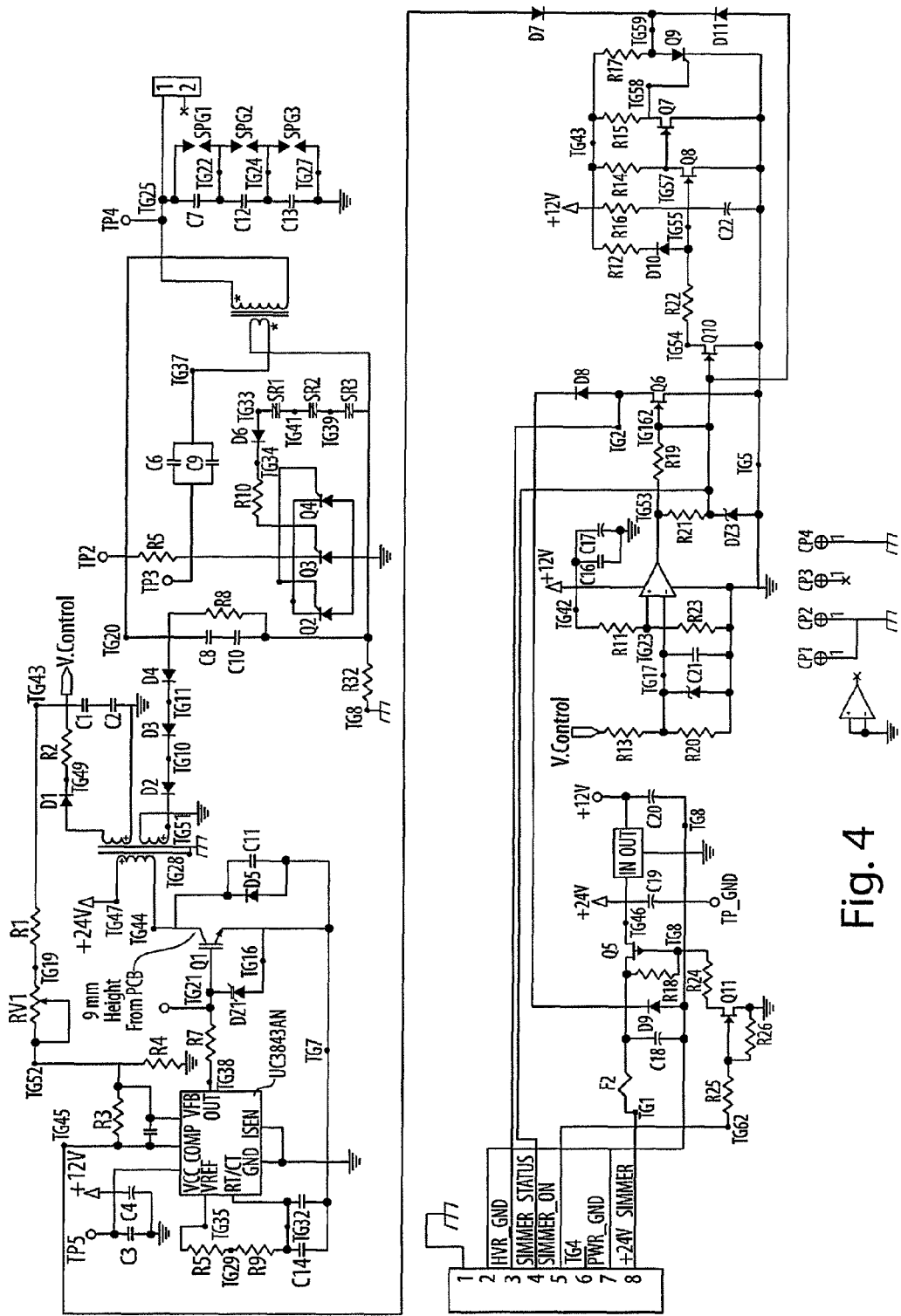
FIG. 4 is a circuit schematic diagram of a simmer board module.

Referring to FIG. 4, an electrical circuit diagram of an implementation of the simmer board 110 is shown. As noted, the simmer board module is configured to trigger the radiation source by providing it, for example, with low standby current that is sufficient to get the radiation source in condition to perform for radiation emission that is subsequently caused by directing high currents through the radiation source. For example, in circumstances in which the radiation source includes a Xenon flash lamp, the simmer board regulates and causes low current to be directed through the Xenon lamp to thus cause the Xenon-based gas mixture within the flash-lamp's tube to become ionized (which decreases the resistance of the gas mixture) and to thus enable high current to travel through the tube. Subsequently, upon delivery of high current to the Xenon flash lamp (i.e., through operation of the current regulation unit 120 and the driver unit 130, as described herein), an Intense Pulsed Light is generated and emitted. As shown, the simmer board includes a flyback converter circuit (comprising the Pulse Width Modulator marked U1 and the transistor Q1) configured to generate a high voltage pulse (e.g., 1600V) to cause an initial spark that is applied to the radiation source, e.g., the IPL source, to cause it to become conductive. After the radiation source has become conductive, low current (e.g., 300-400 mili-ampers) is maintained in the lamp so that it can be controlled to generate light radiation in the manner described herein.

Figure 5:
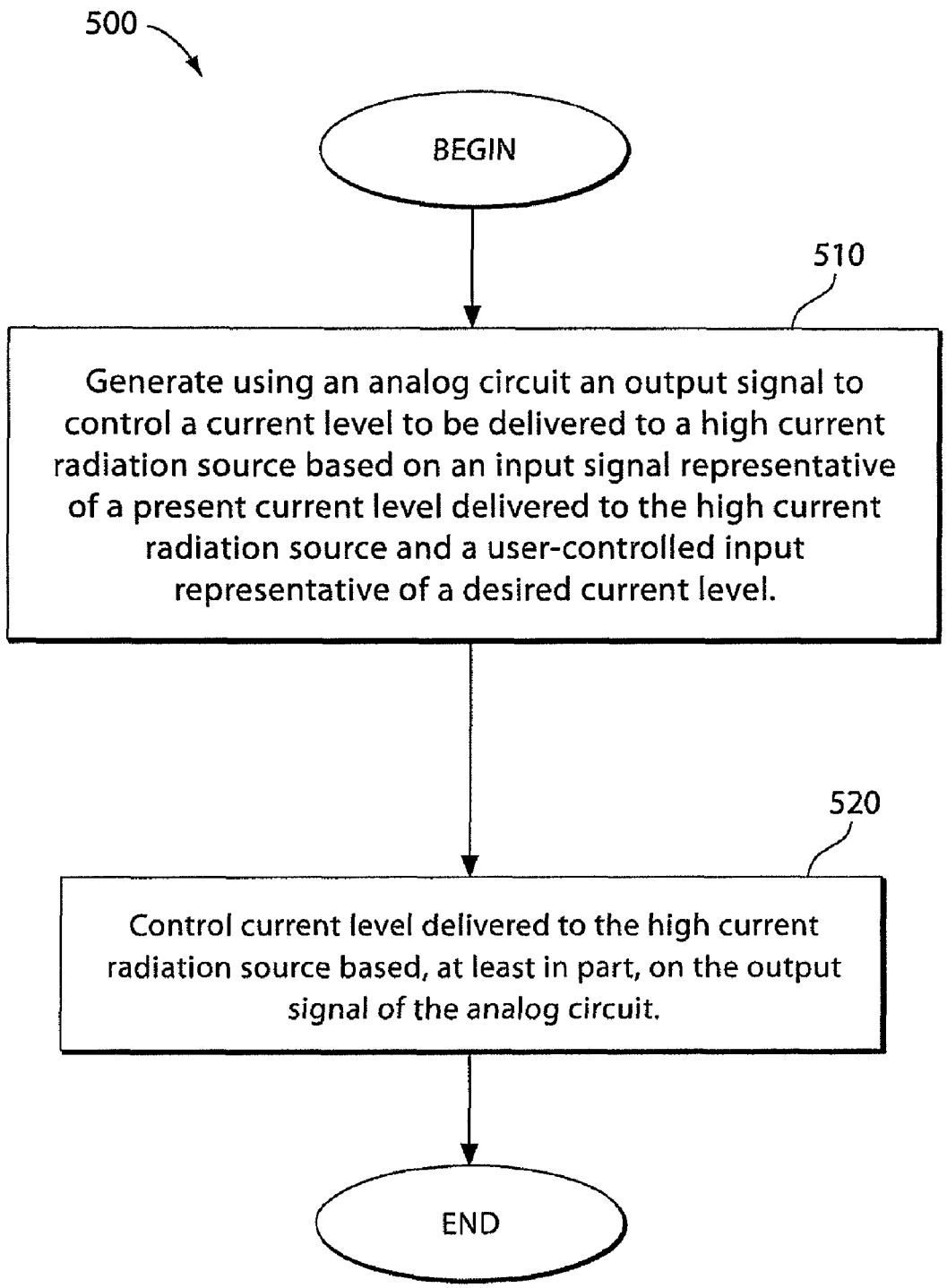
FIG. 5 is a flowchart of a procedure to regulate the current level delivered to a high current radiation source.

Referring to FIG. 5, a flowchart of a procedure 500 to regulate the current level delivered to a high current radiation source is shown. To regulate the current delivered to the radiation source, an output signal to control the current delivered to the radiation source is generated 510 by an analog circuit (e.g., a circuit implemented using one or more operational amplifiers). The analog circuit does not include, for example, any programmable devices/components. The output control signal is generated based on, at least in part, an input signal representative of the present current level of the high current radiation source and a user-controlled input representative of the desired current level. The analog circuit used to generate the output control circuit may be similar to the implementation depicted in FIGS. 2A and 2B.

Based, at least in part, on the output control signal generated by the analog circuit, the current level delivered to the high current radiation source is controlled 520. In some embodiments, this may include actuating a power transistor (such as an IGBT device) using the control output signal generated by the analog circuit to enable or disable the flow of current through the power transistor to the high current radiation source.

A number of embodiments of the invention have been described. Nevertheless, it will be understood that various modifications may be made without departing from the spirit and scope of the invention. Accordingly, other embodiments are within the scope of the following claims.

What is claimed is:

1. A high current radiation system, the system comprising:
a high current radiation source to generate radiation having an output spectrum based, at least in part, on level of current delivered to the radiation source;
an analog circuit to receive an input signal representative of present current level delivered to the high current radiation source and an other input representative of a desired current level, the analog circuit further configured to generate, based, at least in part, on the input signal representative of the present current level delivered to the high current radiation source and the other input representative of the desired current level, an output signal to control the level of the current delivered to the high current radiation source; and
a current driver to control the current delivered to the high current radiation source based, at least in part, on the output signal of the analog circuit;
wherein the analog circuit comprises: an analog comparator;
wherein the analog comparator is configured to:
generate a first logical signal when a voltage level of the other input exceeds a voltage level of the input signal representative of the present current level delivered to the high current radiation source; and
generate a second logical signal when the voltage level of the other input is below the voltage level of the input signal representative of the present current level delivered to the high current radiation source.

2. The system of claim 1, wherein the high current radiation source comprises one or more of: an Intense Pulsed Light (IPL) device, and a laser device.

3. A high current radiation system, the system comprising:
a high current radiation source to generate radiation having an output spectrum based, at least in part, on level of current delivered to the radiation source;
an analog circuit to receive an input signal representative of present current level delivered to the high current radiation source and an other input representative of a desired current level, the analog circuit further configured to generate, based, at least in part, on the input signal representative of the present current level delivered to the high current radiation source and the other input representative of the desired current level, an output signal to control the level of the current delivered to the high current radiation source; and a current driver to control the current delivered to the high current radiation source based, at least in part, on the output signal of the analog circuit;

wherein the current driver comprises a power transistor to enable flow of high current level provided from a power source to the radiation source when the power transistor is actuated by a first logical signal, and to disable current flow through the power transistor when the power transistor is actuated by a second logical signal.

4. The system of claim 3, wherein the power transistor comprises an Insulated-Gate Bi-Polar Transistor (IGBT).

5. The system of claim 1, further comprising:

a sensor to measure the present current level delivered to the radiation source;

wherein the input signal representative of the present current level delivered to the radiation source is generated, at least in part, based on the present current level delivered to the radiation source measured by the sensor.

6. The system of claim 1, further comprising a simmer board to trigger the radiation source.

7. A high current radiation system, the system comprising:

a high current radiation source to generate radiation having an output spectrum based, at least in part, on level of current delivered to the radiation source;

an analog circuit to receive an input signal representative of present current level delivered to the high current radiation source and an other input representative of a desired current level, the analog circuit further configured to generate, based, at least in part, on the input signal representative of the present current level delivered to the high current radiation source and the other input representative of the desired current level, an output signal to control the level of the current delivered to the high current radiation source; and a current driver to control the current delivered to the high current radiation source based, at least in part, on the output signal of the analog circuit;

wherein the analog circuit is implemented without any programmable devices.

8. A method to regulate level of current delivered to a high-current radiation source, the method comprising:

receiving, at an analog circuit, an input signal representative of present current level delivered to the high current radiation source and another input representative of a desired current level;

generating, using the analog circuit, an output signal to control the level of the current delivered to the high current radiation source based on the input signal representative of the present current level delivered to the high current radiation source and the other input representative of the desired current level; and controlling the current delivered to the high current radiation source based, at least in part, on the output signal of the analog circuit, the radiation source generating radiation having an output spectrum based, at least in part, on level of current delivered to the radiation source;

wherein generating, using the analog circuit, the output signal comprises:

generating, using an analog comparator, the output signal to control the current delivered to the high current radiation source;

wherein generating, using the comparator, the output signal comprises:

generating a first logical signal when a voltage level of the other input exceeds a voltage level of the input signal representative of the present current level delivered to the high current radiation source; and generating a second logical signal when the voltage level of the other input is below the voltage level of the input signal representative of the present current level delivered to the high current radiation source.

9. The method of claim 8, wherein the high current radiation source comprises one or more of: an Intense Pulsed Light (IPL) device, and a laser device.

10. A method to regulate level of current delivered to a high-current radiation source, the method comprising:

receiving, at an analog circuit, an input signal representative of present current level delivered to the high current radiation source and another input representative of a desired current level;

generating, using the analog circuit, an output signal to control the level of the current delivered to the high current radiation source based on the input signal representative of the present current level delivered to the high current radiation source and the other input representative of the desired current level; and controlling the current delivered to the high current radiation source based, at least in part, on the output signal of the analog circuit, the radiation source generating radiation having an output spectrum based, at least in part, on level of current delivered to the radiation source;

wherein controlling the current comprises:

actuating a power transistor to control the current flow from a power source to the high current radiation source using the generated output signal such that the current flow from the power source is enabled when the actuating signal is a first logical signal and the current flow from the power source is disabled when the actuating signal is a second logical signal.

11. The method of claim 10, wherein actuating the power transistor comprises: actuating an Insulated-Gate Bi-Polar Transistor (IGBT).

12. The method of claim 8, further comprising:

measuring, using a sensor, the present current level delivered to the radiation source;

wherein the input signal representative of the present current level delivered to the radiation source is generated, at least in part, based on the present current level delivered to the radiation source measured by the sensor.

13. The method of claim 8, further comprising: triggering the radiation source using a simmer board.

14. A method to regulate level of current delivered to a high-current radiation source, the method comprising:

receiving, at an analog circuit, an input signal representative of present current level delivered to the high current radiation source and another input representative of a desired current level;

generating, using the analog circuit, an output signal to control the level of the current delivered to the high current radiation source based on the input signal representative of the present current level delivered to the high current radiation source and the other input representative of the desired current level; and controlling the current delivered to the high current radiation source based, at least in part, on the output signal of the analog circuit, the radiation source generating radiation having an output spectrum based, at least in part, on level of current delivered to the radiation source;

wherein the analog system is implemented without one or more programmable devices.

* * * * *